US00PP36875P2

(12) United States Plant Patent
Lee

(10) Patent No.: US PP36,875 P2
(45) Date of Patent: Aug. 5, 2025

(54) ***RHODODENDRON* PLANT NAMED 'ROBLEZG'**

(50) Latin Name: ***Rhododendron* hybrid**
Varietal Denomination: ROBLEZG

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/935,721

(22) Filed: Nov. 4, 2024

(51) Int. Cl.
*A01H 6/36* (2018.01)
*A01H 5/02* (2018.01)

(52) U.S. Cl.
USPC ..... Plt./238

(58) Field of Classification Search
USPC ..... Plt./238
CPC ..... A01H 6/364; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Rhododendron* plant named 'ROBLEZG' is disclosed, characterized by unique single, flowers colored Red-Purple 61C with a slight sheen of N57C and a distal petal blotch composed of linear dots colored Red 60A. Plants have superior landscape qualities and tolerance to pests. Flowering recurs intermittently from early Spring through Fall. The new cultivar is a *Rhododendron*, suitable for ornamental garden purposes.

1 Drawing Sheet

Latin name of the genus and species: *Rhododendron* hybrid.

Variety denomination: 'ROBLEZG'.

BACKGROUND OF THE INVENTION

The new cultivar is a product of a planned breeding program by the inventor to develop new *Rhododendron* varieties with dark flower color, repeat blooming, all-around sturdiness, pest resistance and diverse environmental adaptability. The seed and pollen parents were unnamed, unpatented proprietary *Rhododendron* seedlings selected for the desired traits listed previously. The open field hand-pollination resulting in the new cultivar was made during 2012 at a nursery in Independence, Louisiana.

*Rhododendron* 'ROBLEZG' was found and selected in 2016 at the same nursery in Independence, Louisiana. The first asexual propagation occurred in the Fall of 2016 by softwood vegetative cuttings at the same nursery. 'ROBLEZG' has been found to retain its distinctive characteristics through successive asexual propagations over multiple generations.

SUMMARY OF THE INVENTION

The cultivar 'ROBLEZG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROBLEZG'. These characteristics in combination distinguish 'ROBLEZG' as a new and distinct *Rhododendron* cultivar:

1. Single, self-cleaning flowers with unique red-purple coloring.

2. Repeat blooming in spring, summer and fall.
3. Superior landscape qualities; tolerant to environmental and climatic conditions.
4. Tolerant to pests.
5. Strong root system.

COMPARISON TO PARENT VARIETIES

Parent comparisons are unavailable as seed was bulk collected and exact parents cannot be identified.

COMMERCIAL COMPARISON

'ROBLEZG' can be compared to the commercial variety *Rhododendron* 'ROBLEZN', U.S. Plant patent application Ser. No. 18/935,725. Plants of the new cultivar 'ROBLEZG' are similar to plants of 'ROBLEZN' in most horticultural characteristics. Plants of the new cultivar 'ROBLEZG', however, differ in the following:

1. Mature upper petal color of 'ROBLEZG' is Red-Purple 61C with a slight sheen of N57C and a distal petal blotch composed of linear dots colored Red 60A. Mature upper petal color of 'ROBLEZN' is Red-Purple 71A with an overall flush of N74B. Central petal section is irregularly dotted Greyed-Purple N186D.
2. Young branches of 'ROBLEZG' are colored Yellow-Green 144B; young branches of 'ROBLEZN' are colored Greyed-Orange 165B.
3. Flowers of 'ROBLEZG' are 3.8 cm long and 6.8 cm in diameter (on average); flowers of 'ROBLEZN' are 5 cm long and 8.5 cm in diameter (on average).

BRIEF DESCRIPTION OF THE PHOTOGRAPH

'ROBLEZG' is illustrated by the accompanying photograph, which shows the flowering plant of 'ROBLEZG' in a one-gallon container at approximately 1-year old. The colors shown are as true as can be reasonably obtained by conventional photographic procedures. Colors in the photograph may differ slightly from the color values cited in the detailed botanical description, which accurately describes the new hybrid *Rhododendron.*

DETAILED BOTANICAL DESCRIPTION

The following is a detailed description of the botanical characteristics of the new and distinct *Rhododendron* 'ROBLEZG'. The detailed description was taken of a 1-year-old one-gallon container plant grown in Loxley, AL in 2024. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'ROBLEZG'.

ROOTS

Root description: Fine, fibrous young roots, well branched. Colored near RHS Grey-Brown 199A.

PLANT

Plant type: Flowering evergreen shrub.
Growth habit: Upright.
Height: Approximately 25 cm to top of foliar and flowering plane.
Width: Approximately 30 cm.
Growth rate: Moderate.
Vigor: Moderate.
Branching characteristics: Moderately well-branched, average 4 to 5 primary branches from the center of the plant. Branches occur at approximately 35° to 60° angles.
Length of primary branches: Average range 7 to 12 cm.
Diameter of primary branches: Average range 5 mm to 7 mm.
Primary branch strength: Very strong, difficult to break.
Primary branch color:
- *Young branches.*—Near RHS Yellow-Green 144B, covered in hirsute hairs colored Greyed-Red 178D.
- *Woody branches.*—Near RHS Grey-Brown N199B, streaked Grey-Green 197A.

Primary branch texture:
- *Immature growth.*—Hirsute.
- *Older growth.*—Slightly scaly.

Lateral branches:
Number of lateral branches: Approximately 2 to 4 per primary branch.
Length of lateral branches: Average 6 cm to 12 cm.
Diameter of lateral branches: Average 4 mm.
Lateral branch strength: Very strong, flexible.
Lateral branch color: RHS Greyed-Red 178A.
Lateral branch texture: Lightly scaly.
Internode length: Average range 1.2 cm to 3.0 cm.

FOLIAGE

Leaf:
- *Type.*—Simple.
- *Arrangement.*—Alternate.
- *Length.*—Approximately 3.2 cm excluding petiole.
- *Width.*—Approximately 2.0 cm.
- *Shape.*—Obovate.
- *Apex.*—Mucronate.
- *Base.*—Attenuate.
- *Attachment.*—Stalked.
- *Margin.*—Entire.
- *Texture of top surface.*—Rough.
- *Texture of bottom surface.*—Rough.
- *Appearance of top surface.*—Glossy.
- *Appearance of bottom surface.*—Matte.
- *Color.*—Young foliage upper side: Near RHS Green 143A. Young foliage under side: Near RHS Green 143C. Mature foliage upper side: Near RHS Green 139A. Mature foliage under side: Near RHS Green 137C.

Venation:
- *Type.*—Pinnate.
- *Venation color upper side.*—Near RHS Yellow-Green N144B.
- *Venation color under side.*—Near RHS Yellow-Green N144D.

Petiole:
- *Length.*—About 5 mm.
- *Diameter.*—About 2 mm.
- *Color.*—Upper Surface: Near RHS Yellow-Green N144D. Lower Surface: Near RHS Yellow-Green 144C.
- *Texture of top surface.*—Glabrous.
- *Texture of bottom surface.*—Hirsute.

FLOWER

Natural flowering season: Intermittently from early Spring through Fall.
Arrangement: Axillary clusters of single open funnel shaped individual flowers. Typically 3 to 5 flowers per cluster.
Inflorescence:
- *Height.*—Average 8.0 cm.
- *Diameter.*—Average 14 cm.
- *Shape.*—Flattened irregular globular.

Peduncle: No peduncle, cluster of flowers emerges directly from top node.
Pedicel:
- *Length.*—Average 1 cm.
- *Diameter.*—4 mm.
- *Color.*—Near RHS Green 138D, heavily flushed Red-Purple 60C.
- *Texture.*—Densely pubescent. Hairs appressed, colored RHS White N155D.
- *Aspect.*—Straight. Approximately 15° angle from stem.

Flowers:
- *Length.*—Average 3.8 cm.
- *Diameter.*—Average 6.5 cm.
- *Aspect.*—Outward facing.
- *Persistence.*—Self-cleaning.
- *Fragrance.*—None detected.

Tube:
- *Length.*—Average 14 mm.
- *Width a widest point.*—Approximately 1.0 cm.
- *Width and narrowest point.*—Approximately 7 mm.

Petals:
- *Quantity.*—5.
- *Unfused petal segments.*—Length: Approximately 2.5 cm. Width: Approximately 2.2 cm.
- *Apex.*—Rounded.

*Shape*.—Unfused portion, obovate.

*Margin*.—Entire. Very slightly ruffled.

*Arrangement*.—Very slightly overlapping, bilateral symmetry dissecting bottom petal. Petals fused approximately ⅓ fused from base.

*Texture*.—Smooth, all surfaces.

*Color*.—Upper surface at first opening: RHS Red-Purple 71A, slight sheen of 72C. Upper most petal basal blotch composed of linear dots colored Red 60A. Under surface at first opening: RHS Red-Purple 72C. Inner surface at maturity: RHS Red-Purple 61C, slight sheen of N57C. Upper most petal basal blotch composed of linear dots colored Red 60A. Outer surface at maturity: RHS Red-Purple 71A, slight sheen of N57B. Upper surface at fading: RHS Red-Purple 59C, slight sheen of N57B. Upper most petal basal blotch composed of linear dots colored Red 60A. Under surface at fading: RHS Red-Purple 71A, strong sheen of N57A.

Bud:

*Shape*.—Elliptic.

*Length*.—4.5 cm.

*Diameter*.—1.5 cm.

*Color*.—RHS Red-Purple 72A, lower 1/3 colored Red-Purple 71D.

Sepals:

*Quantity per flower*.—5.

*Shape*.—Narrow deltate.

*Length*.—4 to 8 mm.

*Width*.—3 mm.

*Apex*.—Acute.

*Base*.—Fused.

*Margin*.—Entire.

*Texture*.—Highly pubescent, hairs appressed.

*Color*.—Inner Surface: Near RHS Yellow-Green 145B. Outer Surface: Near RHS Yellow-Green 145C, flushed Red 61A at base.

REPRODUCTIVE ORGANS

Stamens:

*Number*.—5.

*Length*.—3.8 cm.

*Filament color*.—RHS Red-Purple 68A, upper ⅕ N74B.

*Protrusion*.—Moderate.

*Anthers*.—Length: Approximately 3 mm. Color: Near RHS Greyed-Purple N187A. Pollen: Not observed.

Pistil:

*Number*.—1.

*Length*.—4 cm.

*Style*.—Length: Average 3.5 cm. Color: Lower half near RHS Red-Purple 67C, upper half near Red-Purple 57A.

*Stigma*.—Shape: Globular. Color: Near RHS Red-Purple N57A.

*Ovary*.—Length: 7 mm. Diameter: Approximately 4 mm. Texture: Sericeous. Color: Near RHS Yellow-Green 144C.

OTHER CHARACTERISTICS

Fruit and seed: Not observed.

Disease and pest resistance: Field observations show tolerance to typical pests of *Rhododendron*, which include lace wings (*Stephanitis rhododendri*) and red mites (*Oligonychus ilicis*). The new cultivar did not show susceptibility to root diseases (*Phytophthora*, spp.) observed in other cultivars in the same field test.

Temperature tolerance: USDA Zones 6-10.

What is claimed is:

1. A new and distinct cultivar of *Rhododendron* plant named 'ROBLEZG' as herein illustrated and described.

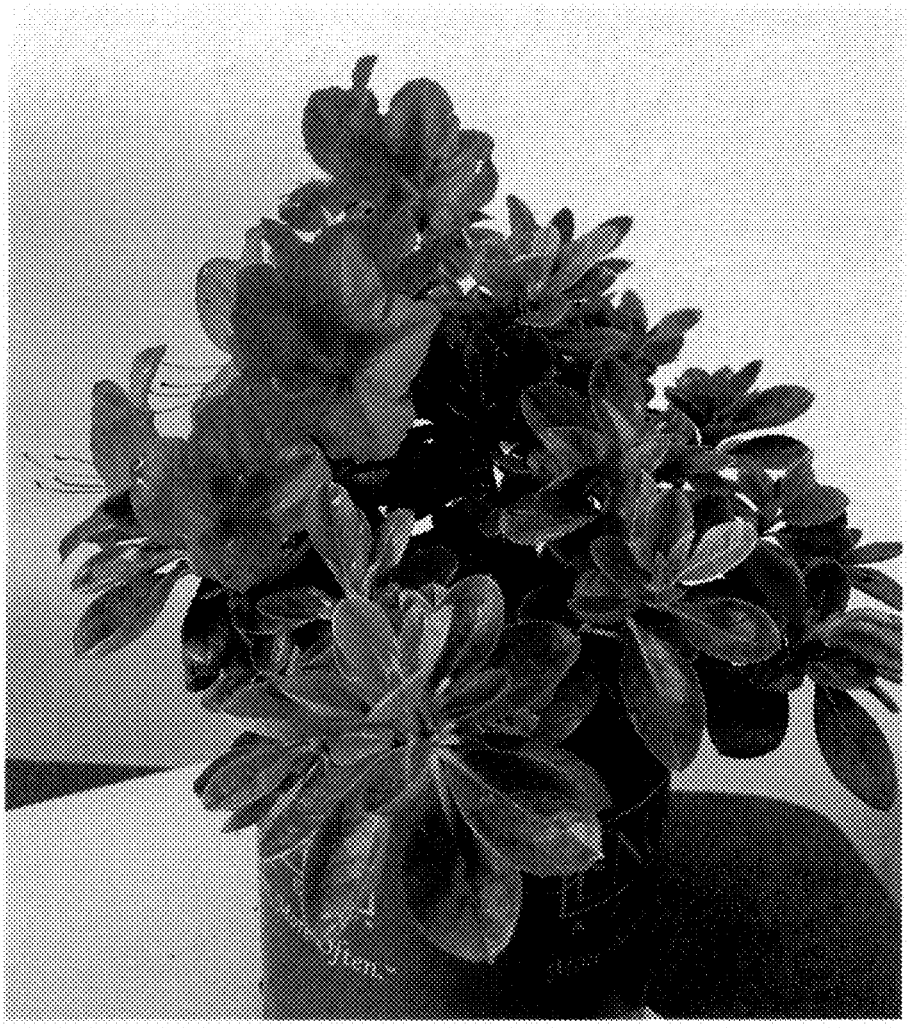

* * * * *